(12) United States Patent
Bishop et al.

(10) Patent No.: US 7,759,537 B2
(45) Date of Patent: Jul. 20, 2010

(54) MULTI LAYERED WOUND DRESSING

(75) Inventors: Stephen M. Bishop, Deeside (GB); Bryan Griffiths, Upton (GB); Patrick G. Linnane, Ellesmere Port (GB); Michael J. Lydon, Sychdyn (GB); Helen Shaw, Widnes (GB)

(73) Assignee: ConvaTec Technologies Inc., Las Vegas, NV (US)

( * ) Notice: Subject to any disclaimer, the term of this patent is extended or adjusted under 35 U.S.C. 154(b) by 919 days.

(21) Appl. No.: 11/055,931

(22) Filed: Feb. 11, 2005

(65) Prior Publication Data

US 2005/0182347 A1    Aug. 18, 2005

(30) Foreign Application Priority Data

Feb. 13, 2004  (GB) ................. 0403245.4
Mar. 15, 2004  (GB) ................. 0405769.1

(51) Int. Cl.
  *A61F 13/00*  (2006.01)
  *A61F 13/15*  (2006.01)
(52) U.S. Cl. .................. 602/43; 604/304; 604/367
(58) Field of Classification Search ............ 602/41–46, 602/52, 58; 604/304–308, 367, 385.01; 128/888–889
See application file for complete search history.

(56) References Cited

U.S. PATENT DOCUMENTS

| | | | | |
|---|---|---|---|---|
| 3,062,209 A * | 11/1962 | Stowasser | ................ | 602/48 |
| 4,196,281 A | 4/1980 | Heart et al. | | |
| 4,246,221 A | 1/1981 | McCorsley, III | | |
| 4,649,909 A | 3/1987 | Thompson | | |
| 4,840,840 A * | 6/1989 | Flynn et al. | ................ | 442/391 |
| 4,875,473 A * | 10/1989 | Alvarez | ................ | 602/58 |
| 4,909,244 A | 3/1990 | Quarfoot et al. | | |
| 5,486,158 A | 1/1996 | Samuelsen | | |
| 5,512,041 A * | 4/1996 | Bogart | ................ | 602/58 |
| 5,571,079 A | 11/1996 | Bello et al. | | |
| 5,607,388 A * | 3/1997 | Ewall | ................ | 602/58 |
| 5,681,579 A * | 10/1997 | Freeman | ................ | 424/448 |
| 5,695,777 A | 12/1997 | Donovan et al. | | |
| 5,968,001 A | 10/1999 | Freeman | | |
| 6,191,335 B1 * | 2/2001 | Robinson | ................ | 602/41 |
| 6,552,244 B1 * | 4/2003 | Jacques et al. | ................ | 602/43 |
| 6,566,575 B1 * | 5/2003 | Stickels et al. | ................ | 602/41 |
| 2002/0038099 A1 | 3/2002 | Griffiths et al. | | |
| 2003/0180346 A1 * | 9/2003 | Woods | ................ | 424/446 |
| 2005/0226917 A1 * | 10/2005 | Burton | ................ | 424/445 |
| 2006/0253058 A1 * | 11/2006 | Evans | ................ | 602/41 |

FOREIGN PATENT DOCUMENTS

| | | |
|---|---|---|
| EP | 0130061 | 8/1988 |
| EP | 0304536 | 3/1989 |
| EP | 0441418 A2 | 8/1991 |

(Continued)

*Primary Examiner*—Patricia M Bianco
*Assistant Examiner*—Tarla R Patel
(74) *Attorney, Agent, or Firm*—John M. Kilcoyne

(57) ABSTRACT

A multi layered wound dressing for use on wounds producing high levels of exudate, the dressing comprising a transmission layer having a high MVTR; an absorbent core capable of absorbing and retaining exudates; and a wound contacting layer which transmits exudate to the absorbent core, the absorbent core and wound contacting layer limiting the lateral spread of exudate in the dressing to the region of the wound.

26 Claims, 8 Drawing Sheets

FOREIGN PATENT DOCUMENTS

| | | |
|---|---|---|
| EP | 0092999 B1 | 4/1992 |
| EP | 0301874 B1 | 6/1992 |
| EP | 0433354 B1 | 1/1994 |
| EP | 0476756 B1 | 4/1996 |
| EP | 0680344 B1 | 4/1998 |
| EP | 0892863 B1 | 6/2001 |
| EP | 1314410 A3 | 5/2003 |
| GB | 2380945 A | 4/2003 |
| GB | 2382305 | 5/2003 |
| WO | WO 93/12275 | 6/1993 |
| WO | WO 94/17227 | 8/1994 |
| WO | WO 00/01425 | 1/2000 |
| WO | WO 00/041661 | 7/2000 |
| WO | WO 01/34079 A1 | 5/2001 |
| WO | WO 03/033041 A2 | 4/2003 |

* cited by examiner

MULTI LAYERED WOUND DRESSING

BACKGROUND OF THE INVENTION

The present invention relates to a multi layered wound dressing and particularly, but not exclusively, to a wound dressing with a high fluid handling capacity for use as a dressing for highly exudating wounds.

It is known to make wound dressings for use on heavily exudating wounds from materials with a high moisture vapour transmission rate (MVTR). Such dressings manage exudate by relying on the exudate being taken up by one side of the dressing and transpired through the other side of the dressing. The dressing itself is thus not required to retain large volumes of exudate, Examples of such dressings are ALLEVYN™ marketed in adhesive and non-adhesive versions by Smith and Nephew or TIELLE PLUS™ marketed by Johnson and Johnson. Such dressings are not designed to absorb and retain the exudate but to manage the exudate by allowing the moisture present in the exudate to evaporate.

A dressing said to have a high rate of moisture evaporation is described in EP 304 536A. The dressing disclosed in this document has a flexible hydrophilic layer which absorbs the exudate, sandwiched between two layers of adhesive. The absorbent layer additionally contains a fabric layer which is intended to improve the structural integrity of the dressing once it is exposed to exudate. A disadvantage of such dressings is that the lateral wicking of exudate is not contained and can cause the 'normal' skin surrounding the wound to macerate.

A further disadvantage of such dressings with a high MVTR is that the rapid loss of exudate can cause the wound to become desiccated.

A further disadvantage of known dressings, in particular foam dressings such as ALLEVYN™, is that if pressure is applied to the dressing in use, such as under a compression bandage system, then exudate absorbed by the dressing is often squeezed out of the dressing. Furthermore, the ability of the dressing to absorb exudate is reduced once compression is applied. Such dressings are thus not suitable for use on wounds where compression is required or experienced.

There is thus a need for a wound dressing which is capable of handling high levels of fluid exudate, for example at least 6 g of exudate per 10 $cm^2$ of dressing in 24 hours, which also does not cause appreciable maceration of the skin surrounding the wound, does not allow the wound to become desiccated, and which can be used, if necessary, under compression.

BRIEF SUMMARY OF THE INVENTION

According to a first aspect the invention provides a multi layered wound dressing for use on wounds producing high levels of exudate, the dressing comprising:
 a transmission layer having a high MVTR
 an absorbent core capable of absorbing and retaining exudate
 a wound contacting layer which transmits exudate to the absorbent core, the absorbent core and wound contacting layer limiting the lateral spread of exudate to the region of the wound.

According to a second aspect the invention provides a multi layered wound dressing with a high fluid handling capacity comprising:
 (a) a transmission layer having a high MVTR;
 (b) an adhesive;
 (c) an absorbent core having high absorbency and low lateral wicking; and a wound contacting layer.

Preferably the adhesive is arranged as a layer of adhesive. Preferably the transmission layer overlies the adhesive, which in turn overlies the absorbent core, which in turn overlies the wound contact layer.

An additional keying layer may be included on either the wound facing side of the absorbent core, or the non-wound facing side of the absorbent core, or on both the wound facing and the non-wound facing side of the absorbent core. Preferably a keying layer is located between the absorbent core and the wound contact layer. We have found that this may also give the advantages of binding the wound contact layer to the absorbent core which improves the rate of exudate transport to the absorbent core while reducing lateral wicking. The keying layer also reduces voids between the wound contact layer and absorbent layer which reduces bacterial growth potential.

Wound dressings according to the invention are capable of handling at least 6 g of exudate per 10 $cm^2$ of dressing in 24 hours. Preferably the wound dressing can handle at least 8 g of exudate per 10 $cm^2$ of dressing in 24 hours. Preferably the wound dressing can handle between about 8 g and about 20 g of exudate per 10 $cm^2$ of dressing in 24 hours.

The wound dressing may be self adhesive or non self adhesive.

The wound contact layer is preferably non-adhesive and is configured to transmit exudate to the absorbent core. Preferably the wound contact layer creates a moist environment at the wound surface which is conducive to wound healing and reduces the risk of wound desiccation. Furthermore, the absorption properties of the wound contact layer are preferably not significantly compromised under the compression typically applied by a bandage or equivalent compression device. A bandage may be arranged to apply a pressure of about 40 mm Hg.

Preferably the wound contact layer also absorbs exudate from the wound. The wound contact layer preferably has an absorbency of at least 10 g of sodium chloride and calcium chloride solution (*BP* 1995 *Appendix 1A*) per gram of absorbent layer measured by the absorbency test for alginate dressings *BP* 1195. The wound contact layer is preferably fibrous and most preferably comprised of gel forming fibres.

The gel forming fibres are preferably chemically modified cellulosic fibres in the form of a fabric and in particular carboxymethylated cellulose fibres as described in PCT WO00/01425 to Azko Nobel UK Ltd. The carboxymethylated cellullosic fabrics preferably have a degree of substitution between 0.12 to 0.35 as measured by IR spectroscopy (as defined in WO00/01425) more preferably a degree of substitution of between 0.20 and 0.30 and are made by carboxymethylating a woven or non-woven cellulosic fabric such that the absorbency is increased. Particular preferred fabrics have an absorbency of between 10 g/g of sodium/calcium chloride as defined above to 30 g/g of sodium/calcium chloride as measured by the method defined above. Particularly preferred fabrics have an absorbency of 15 g/g to 25 g/g and most preferred of 15 g/g to 20 g/g of sodium/calcium chloride as measured by the method defined above.

The cellulosic fabric preferably consists solely of cellulosic fibre but may contain a proportion of non-cellulosic textile fibre or gel forming fibre. The cellulosic fibre is of known kind and may comprise continuous filament yarn and/or staple fibre. The carboxymethylation is generally performed by contacting the fabric with an alkali and a carboxymethylating agent such a chloracetic acid in an aqueous system. The fabric is preferably of a non-woven type to reduce shedding in the wound on cutting the dressing. Preferably the fabric is hyrdoentangled and thus comprises a series of apertures on a microscopic scale.

Preferably the wound contact and absorbent layers limit the lateral spread of exudate to the immediate area of the wound so that exudate is not spread across the lateral extent of the layer, but instead remains essentially in the region of the wound. Preferably the wound contact layer has a low lateral wicking rate to limit the spread of exudate. By having a low lateral wicking rate maceration of skin surrounding the wound is reduced. Preferably the lateral wicking rate is from 5 mm per minute to 40 mm per minute, more preferably from 5 to 15 mm per minute.

Preferably the fibre density in the wound contact layer is between 25 gm$^2$ and 55 gm$^2$, more preferably the density is approximately 35 gm$^2$.

Preferably the wound contact layer provides structural integrity to the dressing and physically constrains the absorbent core. In use the wound contact layer can help to physically constrain the gelled absorbent layer which may otherwise have a tendency to delaminate and slide off the dressing.

The absorbent core is present to transport wound fluid away from the wound and absorb exudate while limiting lateral spread. The reduction in lateral spread afforded by a wound dressing of the present invention reduces maceration of skin surrounding the wound. The absorbency and fluid handling properties of the absorbent core are preferably not significantly reduced when the dressing is placed under the kinds of pressure usually experienced by wound dressings such as a compression stocking. Compression stockings are typically applied at about 40 mmHg.

The absorbent core preferably displays a high absorbency of exudate of at least 10 g/g, preferably 15 g/g to 50 g/g and most preferably an absorbency of from 20 g/g to 50 g/g. Absorbency is measured as described above with reference to the wound contact layer.

Preferably the lateral wicking of the absorbent core is low, preferably less the 20 mm per minute. Preferably from 1 mm per minute to 15 mm per minute, more preferably from 1 mm per minute to 10 mm per minute.

The absorbent core is preferably fibrous and most preferably comprises gel forming fibres. The absorbent core is preferably non-woven. We have found that fibrous layers as opposed to polymeric absorbent layers have the advantage that they are especially able to gel block which resists the lateral spread of exudate. In addition, exudate is absorbed rapidly and retained under pressure.

The fibres suitable for use in the absorbent core of the present invention include hydrophilic fibres which upon the uptake of wound exudate become moist and slippery or gelatinous and thus reduce the tendency for the surrounding fibres to adhere to the wound. The fibres can be of the type which retain their structural integrity on absorption of exudate or can be of the type which lose their fibrous form and become a structureless gel or a solution on absorption of exudate.

The gel forming fibres are preferably spun sodium carboxymethylcellulose fibres, chemically modified cellulosic fibres, in particular carboxymethylated fibres as described in PCT WO93/12275 to Courtaulds PLC or GB 93/01258 to Courtaulds PLC, pectin fibres, alginate fibres and particularly those described in WO 94/17227 to E.R Squibb and Sons or EP 433354 to CV Laboratories Ltd or EP 476756 to CV Laboratories Ltd, or composite fibres of alginate and polysaccharide such as those described in EP 0892863 to Bristol-Myers Squibb Company, chitosan fibres, hyaluronic acid fibres, or other polysaccharide fibres or fibres derived from gums. The cellulosic fibres preferably have a degree of substitution of at least 0.05 carboxymethyl groups per glucose unit. The production of solvent-spun cellulose fibres is described for example in U.S. Pat. No. 4,246,221 and U.S. Pat. No. 4,196,281 as well as in PCT WO93/12275 mentioned above.

Preferably the gel forming fibres for use in the present invention have an absorbency of either water or saline of at least 15 g/g as measured in the free swell absorbency method, more preferably at least 25 g/g or 50 g/g. The degree of substitution of the gel forming fibre is preferably at least 0.2 carboxymethyl groups per glucose unit, more preferably between 0.3 and 0.5. The tenacity of the fibre is preferably in the range 25-15 cN/tex.

The absorbent layer may, in addition to the gel forming fibres, also comprise other fibres such as textile fibres which can be natural or synthetic but are preferably cellulosic fibres for example viscose rayon, multi-limbed viscose, cotton, or regenerated cellulose or fibres having a higher absorbency that most textile fibres such as the multi-limbed cellulose fibres as described in EP-A-301874. In general textile fibres absorb liquids by capillary action and are not hygroscopic, this means that their absorbencies as measured by the free swell absorbency test are low, such as less than 1 gram of liquid per gram of fibre.

More preferably the dressing comprises an intimate blend of gel forming fibres and cellulosic fibres. Preferably the blend is in the range of up to 25% cellulosic fibres by weight and 75% to 100% gel forming fibres by weight. More preferably the blend is in the range of up to 50% cellulosic fibres by weight and 50% to 100% gel forming fibres by weight. The blend may be about 50% cellulosic fibres by weight and about 50% gel forming fibres by weight.

The use of a blend of gel forming fibres and cellulosic fibres has the benefit of reducing shrinkage of the dressing when wet, thereby reducing distortion of the dressing which may cause discomfort to the patient. Preferably shrinkage of the dressing is reduced to less than 25%. If the blend is optimised shrinkage can be reduced to less than 15%. Shrinkage is measured as the reduction in the surface area of the wound contact layer. It is thought that the structure and composition of the non gelling fibres maintains the shape of the absorbent core of the wound dressing reducing shrinkage of the dressing in use.

The absorption properties of a dressing according to the invention may in use prevent lateral spread of the dressing, and the expansion of the dressing beyond the edge of a bandage holding the dressing in place.

The fibres suitable for use in the present invention can be processed using conventional textile machinery, for example by the staple route including cutting, carding and needling, and if desired crimping, drafting and spinning.

Preferably the fibre density in the absorbent core is between 150 gm$^2$ and 250 gm$^2$, more preferably the density is approximately 200 gm$^2$.

The adhesive where present serves to hold the layers of the dressing together and may, in a preferred adhesive dressing embodiment, be used to adhere the dressing to the skin. Preferably the adhesive composition comprises a homogenous blend of one or more water soluble hydrocolloids and one or more low molecular weight polyisobutylenes such as are described in EP-B-92999 incorporated herein by reference. The water soluble hydrocolloids may be selected from sodium carboxymethylcellulose, pectin, gelatine, guar gum, locust bean gum, karaya gum, and mixtures thereof. The polyisobutylenes may be selected from low molecular weight polyisobutylenes having a viscosity average molecular weight of from 36,000 to 58,000 (Florey). The adhesive layer is capable of absorbing exudate while maintaining adhesion of the dressing to the skin.

Alternatively the adhesive composition may comprise a homogeneous blend of one or more hydrocolloids, one or more low molecular weight polyisobutylenes, one or more styrene block copolymers, mineral oil, butyl rubber, a tackifier and small amounts of optional components. By selection of specific ranges of the amounts of the above listed components, an adhesive composition may be prepared having good adhesion to the skin and stretchability. Such compositions and the preparation therefore are disclosed in EP-B-130061.

Preferably the adhesive is such that the removal of an adhesive wound dressing is not traumatic to the patient. Preferably the adhesive ensures a secure application of the dressing whist still permitting non-traumatic removal. Non-traumatic dressing removal may be facilitated by using an adhesive which gels slightly upon interaction with a fluid. The gel formation aiding dressing removal.

Alternatively, the adhesive may be a polyamide web.

The transmission layer of the present invention is preferably a layer having a MVTR of at least 300 $gm^2/24$ hours measured by the method described in 1993 *BP Appendix XX J*1 or in the range of from 100 $gm^2/24$ hours to 10000 $gm^2/24$ hours. The transmission layer may be in the form of a film/foam laminate, for example, expanded polyurethane foam laminated to a polyurethane film.

Preferably the transmission layer allows the dressing to be worn whilst the patient bathes or showers without the wound becoming wet.

Preferably the transmission layer has an outer surface which has a low co-efficient of friction, reducing the risk of sheer, that is, lateral friction causing the wound dressing to sheer, and providing a surface that mat be easily wiped clean.

Preferably the transmission layer is a barrier to bacteria, viruses and external contaminants thereby protecting the wound from infection.

The dressing may also comprise additional optional layers such as a soluble medicated film, for example applied to the contact layer or an odour-absorbing layer such as an activated carbon layer.

The dressing may also comprise a spreading layer. The role of the spreading layer is to laterally spread fluid absorbed by the dressing across the high MVTR transmission layer. This layer may be located on the non-wound facing side of the absorbent core. The spreading layer may comprise 100% viscose, polyolefin type fibres or a viscose/polyester blends. More preferably the spreading layer is a viscose/polyester hydroentangled non-woven layer.

The spreading layer may be located between the absorbent core and the adhesive layer. An additional keying layer may be positioned between the spreading layer and the absorbent core or the wound contact layer and the absorbent core.

The keying layer may comprise a thin layer of polyamide web. The keying layer may bond the absorbent core to neighbouring layers, for example, to the wound contacting layer, the adhesive or the spreading layer, so as to improve the structural integrity of the dressing. This layer may also act in use to reduce the risk of the absorbent layer becoming detached from the dressing when moist. The keying layer may reduce delamination of the dressing in use.

The dressing may also comprise an additional adhesive layer on the wound contacting face of the dressing. Preferably this layer is arranged around the outer edge of the wound contacting layer, and the wound dressing as a whole, and provides adhesive to allow the dressing to be adhered to a patient in use whilst leaving a sufficient area of the wound contacting layer exposed for the dressing to be effective when in use. Preferably the adhesive in this additional adhesive layer is as described above.

Preferably a wound dressing according to the present invention has a cuttable structure, thereby allowing versatility of use on a range of anatomical structures.

Preferably the total thickness of the dressing is between 2 mm and 4 mm, more preferably between 2.2 mm and 3.7 mm. This allows the dressing to be more conformable and more discrete in use.

Preferably a dressing according to the present invention can be worn for at least 7 days, more preferably the dressing can be worn for 10 or more days. The high fluid handling capacity means that the dressing can be changed less frequently than dressings which are capable of handling less fluid. The less frequently the dressing is changed the more opportunity the wound has to heal.

According to a second aspect the invention provides a wound dressing have an absorbent core and a fluid handling capacity of at least 6 g of fluid per 10 $cm^2$ of dressing in 24 hours. Preferably the dressing can handle at least 8 g of fluid per 10 $cm^2$ of dressing in 24 hours. Preferably the wound dressing can handle at least between about 8 g and 15 g of fluid per 10 $cm^2$ of dressing in 24 hours. The fluid handling capacity is based on the ability of the dressing to handle sodium chloride and calcium chloride solution (*BP 1995 Appendix 1A*) which it is understood will be handled by the dressing in a manner similar to that in which the dressing handles wound exudate.

According to a third aspect the invention provides an absorbent material comprising about 50% gel forming fibres, such as HYDROCEL™, and about 50% cellulosic fibres, such as LYOCELL™, which has less the 20% shrinkage in surface area in use.

BRIEF DESCRIPTION OF SEVERAL VIEWS OF THE DRAWINGS

Preferred embodiments of the present invention will now be described by way of example with reference to the accompanying drawings, in which.

DETAILED DESCRIPTION OF THE INVENTION

Figure 1:
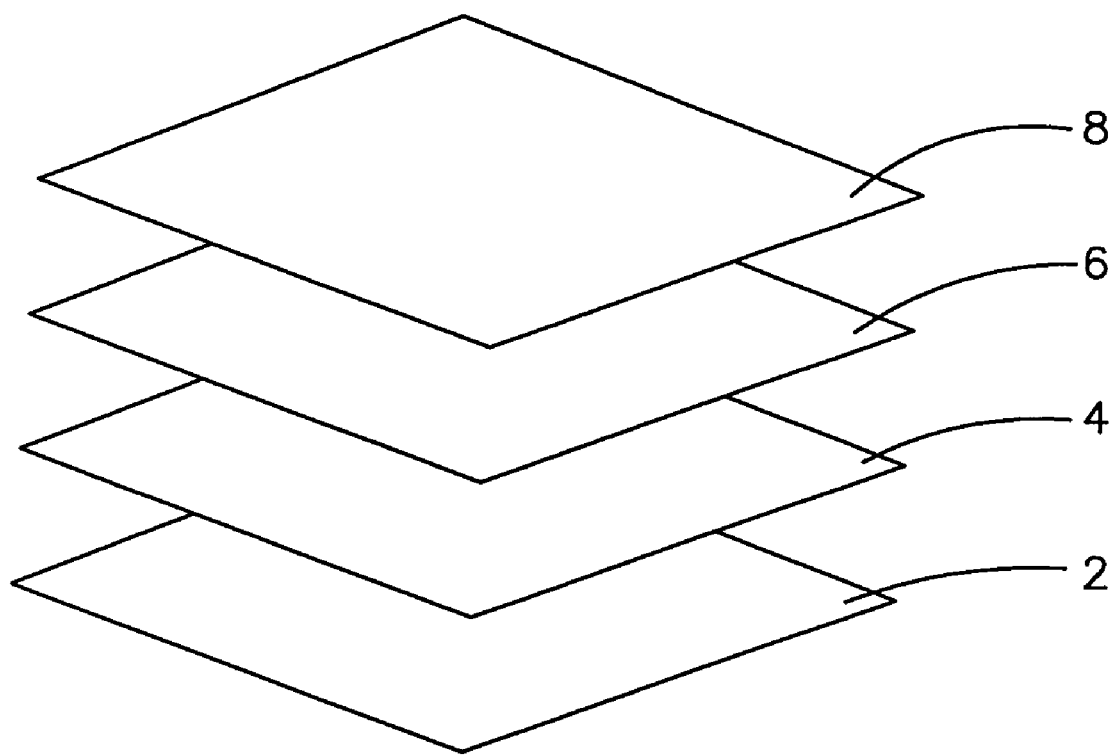
FIG. 1 is a schematic diagram of a non self adherent embodiment of a multi layer wound dressing according to the invention.
Figure 2:
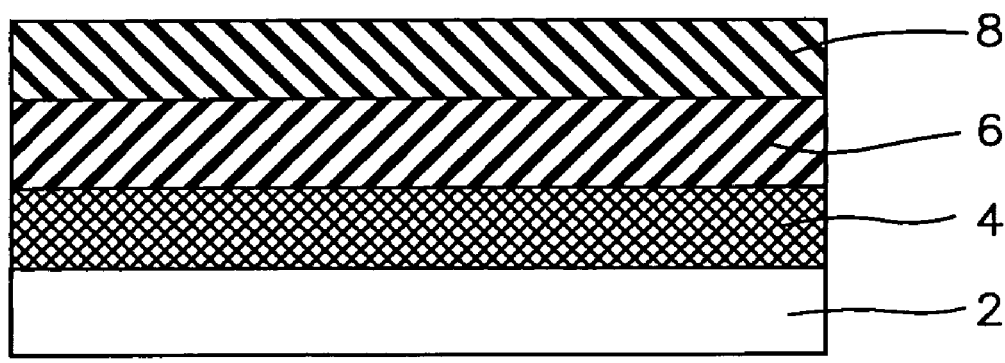
FIG. 2 is a schematic cross sectional view of the dressing of FIG. 1.

Referring now to FIGS. 1 and 2 a non-adhesive multi layered wound dressing according to the invention comprises a transmission layer (2), an adhesive layer (4), an absorbent core (6) and a wound contacting layer (8).

The wound contacting layer is made from 35 gm$^2$ of a non-woven, hyrdoentangled fabric comprising gel forming fibres.

The absorbent core is made from 200 gm$^2$ of a 80/20 blend of cellulose fibres of the viscose rayon type with gel forming fibres such as those described in WO93/12275 and sold as the product HYDROCEL™ (Acordis). In an alternative embodiment the absorbent core is a 75/25 blend of HYDROCEL™ and LYOCELL™. In a yet further embodiment the absorbent core is a 50/50 blend of HYDROCEL™ and LYOCELL™.

The adhesive layer is a blend of one or more water soluble hydrocolloids and one or more low molecular weight polyisobutylenes. In an alternative embodiment the adhesive layer may be a polyamide web.

The transmission layer is a polyurethane foam/film laminate.

Figure 3:
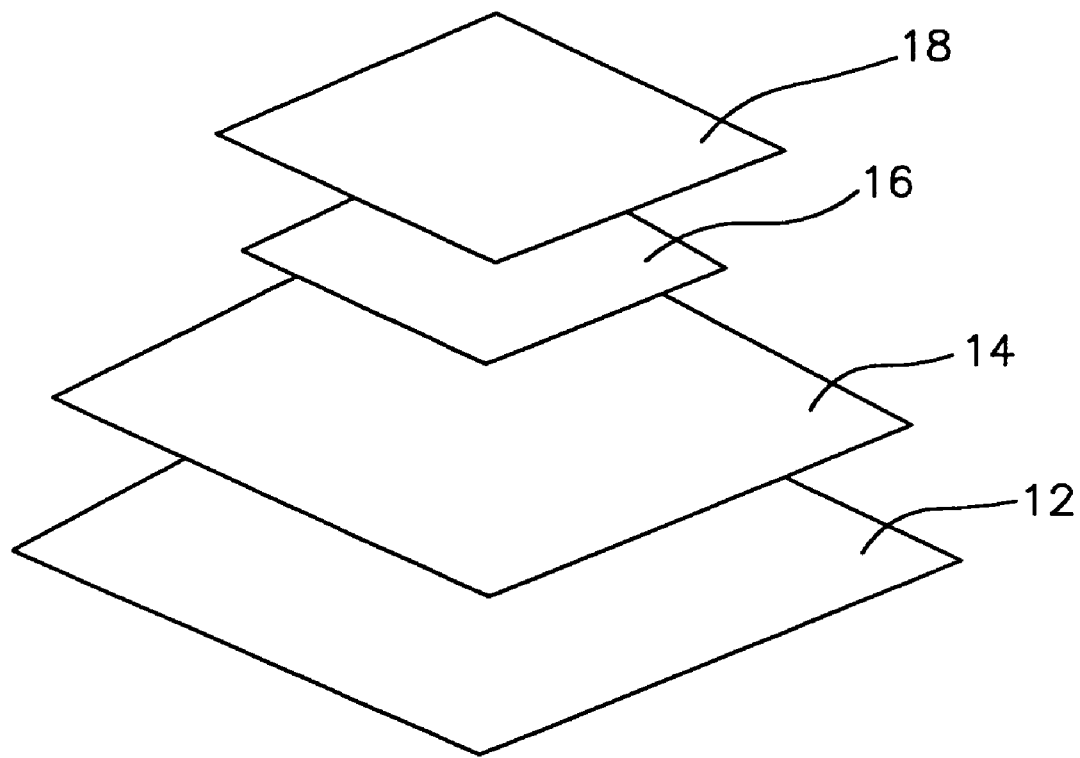
FIG. 3 is a schematic diagram of a self adherent embodiment of a multi layer wound dressing according to the invention.
Figure 4:
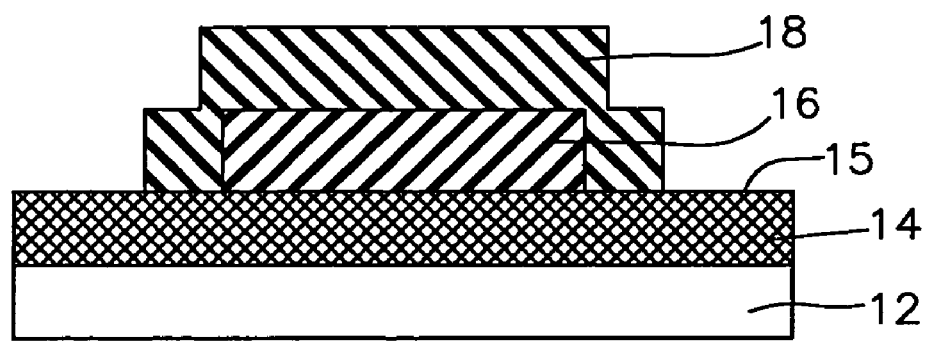
FIG. 4 is a schematic cross sectional view of the dressing of FIG. 3.

Refer now to FIGS. 3 and 4 an adhesive multi layered wound dressing according to the invention comprises a transmission layer (12), an adhesive layer (14), an absorbent core (16) and a wound contacting layer (18). The layers are made of the same materials discussed above with reference to FIGS. 1 and 2. In the adhesive wound dressing of FIGS. 3 and 4 the absorbent core is smaller than the transmission layer and the adhesive layer and is positioned in the centre of the adhesive layer. The adhesive holds the absorbent core in position. The wound contacting layer is larger than the absorbent core but smaller than the adhesive and transmission layer and is positioned over the absorbent core in contact with the absorbent core and the adhesive layer. A peripheral rim (15) of the adhesive layer is left exposed and can be used to adhere the dressing to the skin of a patient.

Figure 5:
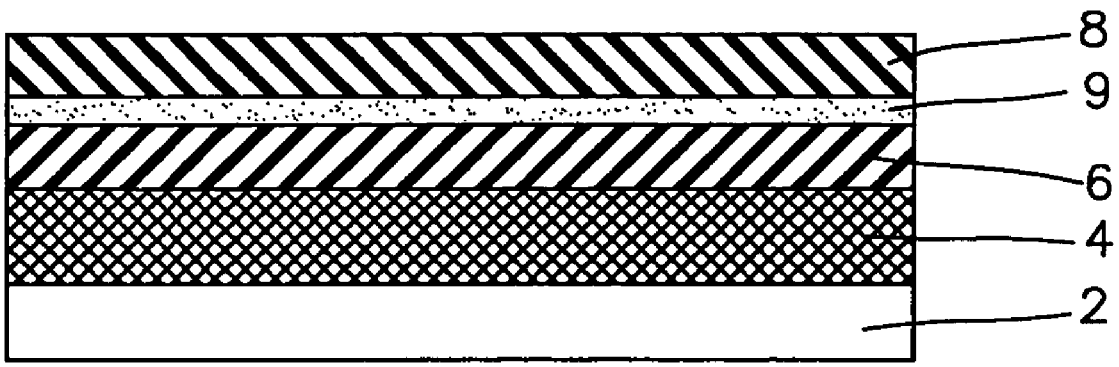
FIG. 5 is a schematic cross sectional view of the dressing of FIG. 2 including an additional keying layer between the wound contacting layer and the absorbent core.
Figure 6:
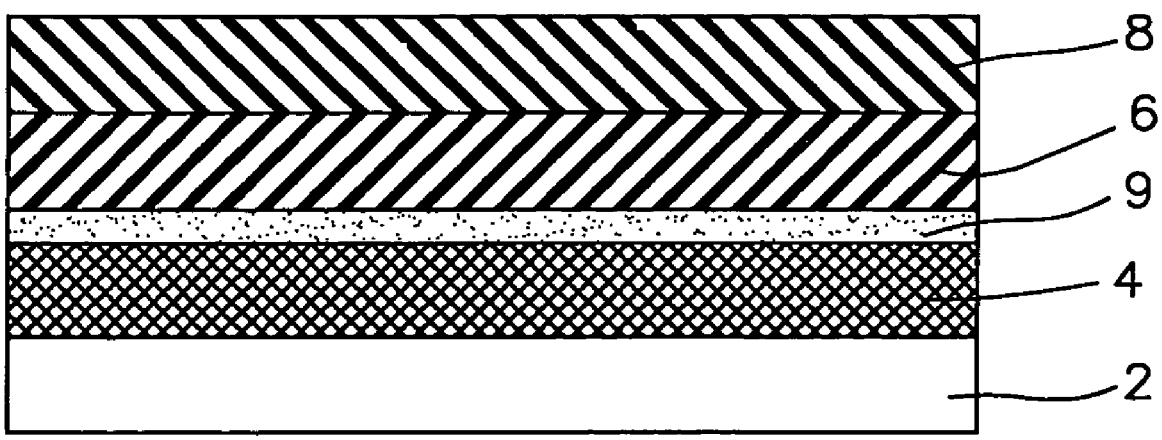
FIG. 6 is a schematic cross sectional view of the dressing of FIG. 2 including an additional keying layer between the adhesive layer and the absorbent core.

FIGS. 5 and 6 are non-adhesive wound dressings, similar to that of FIGS. 1 and 2, with an additional keying layer (9;9') between the wound contact layer (8) and the absorbent core (6), and the wound contact layer (8) and the adhesive layer (4), respectively. The keying layer comprises a polyamide web.

Figure 7:
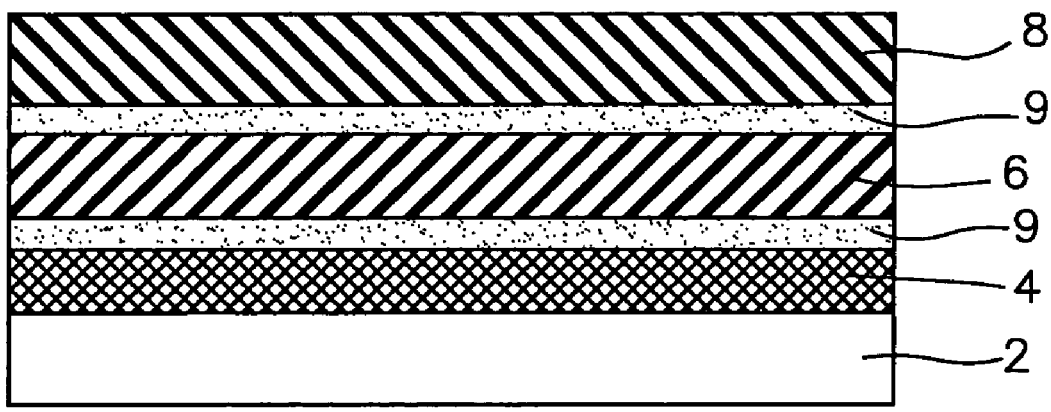
FIG. 7 is a schematic cross sectional view of the dressing of FIG. 2 including an additional keying layer between the wound contacting layer and the absorbent core and between the absorbent core and the adhesive layer.

FIG. 7 is a non-adhesive wound dressing, similar to that of FIGS. 1 and 2, with keying layers (9, 9') between the between the wound contact layer (8) and the absorbent core (6) and between the wound contact layer (8) and the adhesive layer (4).

Figure 8:
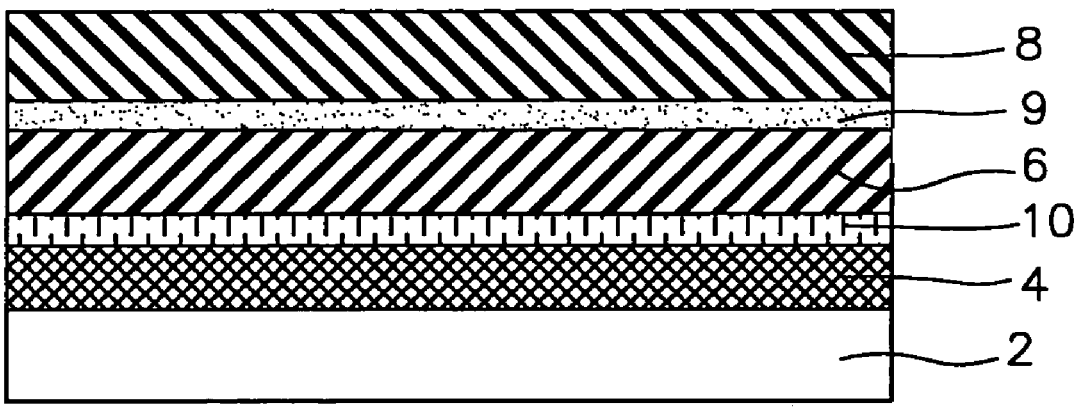
FIG. 8 is a schematic cross sectional view of the dressing of FIG. 5 including an additional spreading layer.

FIG. 8 is a non-adhesive wound dressing including a keying layer (9) between the wound contact layer (8) and the absorbent core (6), and a spreading layer (10) between the absorbent core (6) and the adhesive layer (4). The spreading layer is configured to have the same surface area as the non wound facing face of the absorbent core. The spreading layer comprises a viscose/polyester hydro entangled non-woven fabric.

Figure 9:
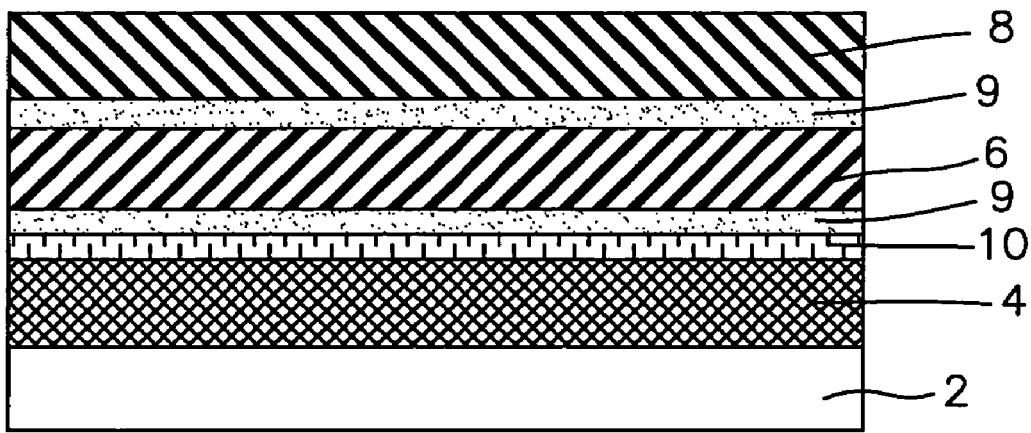
FIG. 9 is a schematic cross sectional view of the dressing of FIG. 7 including an additional spreading layer.

FIG. 9 is a non-adhesive wound dressing including a two keying layers (9, 9') and a spreading layer (10) between the keying layer (9') and the adhesive layer (4).

Figure 10:
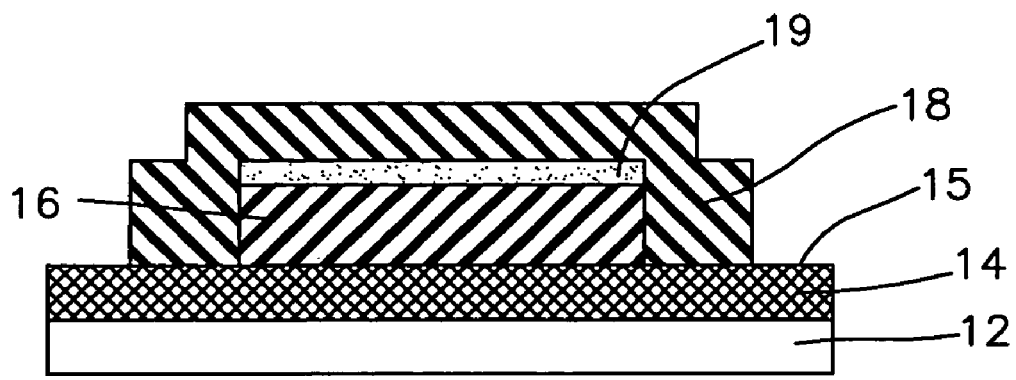
FIG. 10 is a schematic cross sectional view of the dressing of FIG. 4 including an additional keying layer between the wound contacting layer and the absorbent core.
Figure 11:
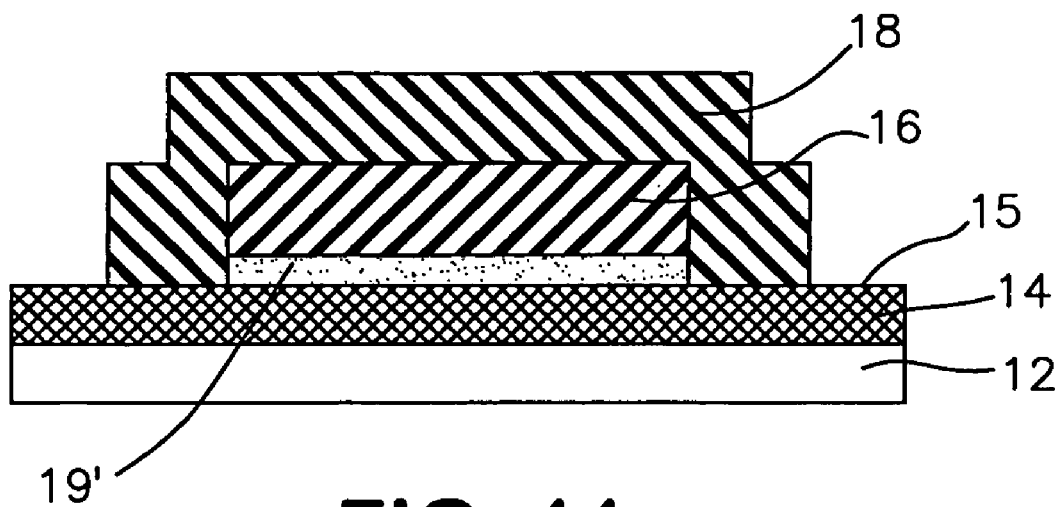
FIG. 11 is a schematic cross sectional view of the dressing of FIG. 4 including an additional keying layer between the absorbent core and the adhesive layer.

FIGS. 10 and 11 are adhesive wound dressings, similar to that of FIGS. 3 and 4, with a keying layer (19;19') between the wound contact layer (18) and the absorbent core (16), and the wound contact layer (18) and the adhesive layer (14), respectively. The keying layer comprises a polyamide web.

Figure 12:
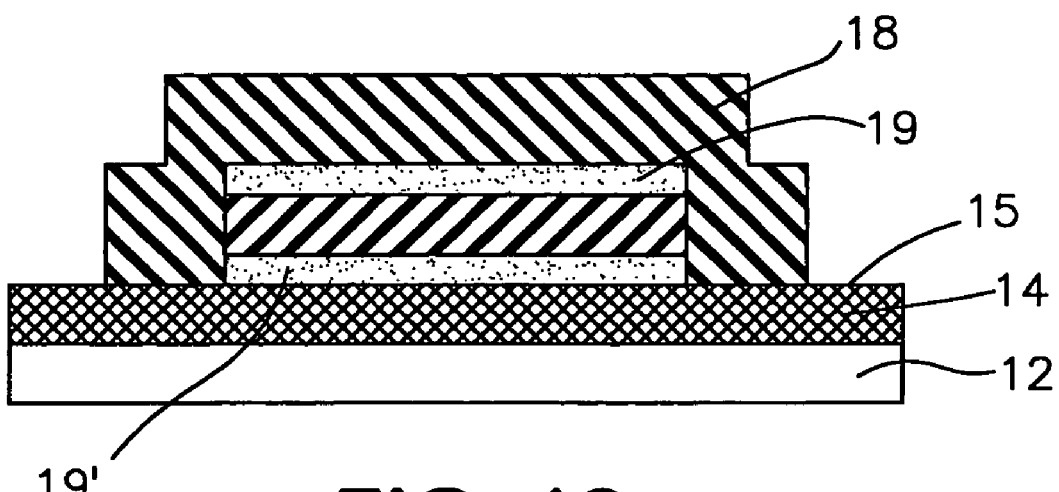
FIG. 12 is a schematic cross sectional view of the dressing of FIG. 4 including an additional keying layer between the wound contacting layer and the absorbent core and between the absorbent core and the adhesive layer.

FIG. 12 is an adhesive wound dressing with keying layers (19, 19') between the between the wound contact layer (18) and the absorbent core (16) and between the wound contact layer (18) and the adhesive layer (14).

Figure 13:
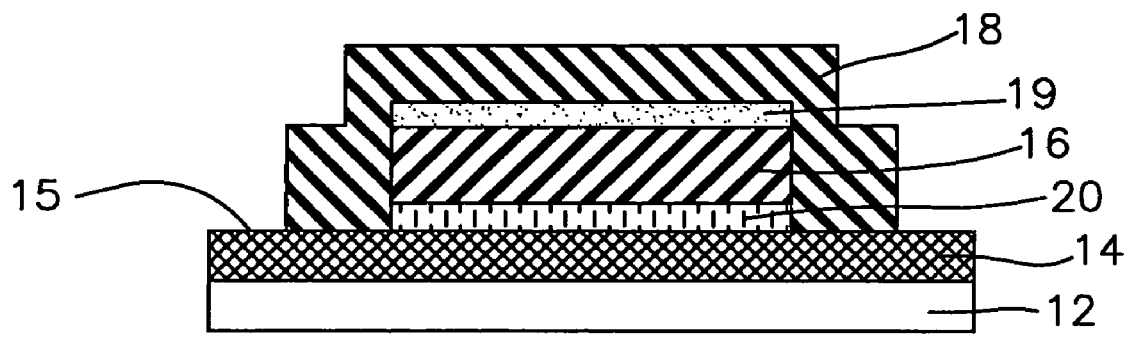
FIG. 13 is a schematic cross sectional view of the dressing of FIG. 10 including an additional spreading layer.

FIG. 13 is an adhesive wound dressing including a keying layer (19) between the wound contact layer (18) and the absorbent core (18), and a spreading layer (20) between the absorbent core (16) and the adhesive layer (14). The spreading layer is configured to have the same surface area as the non wound facing face of the absorbent core. The spreading layer comprises a viscose/polyester hydro entangled non-woven fabric.

Figure 14:
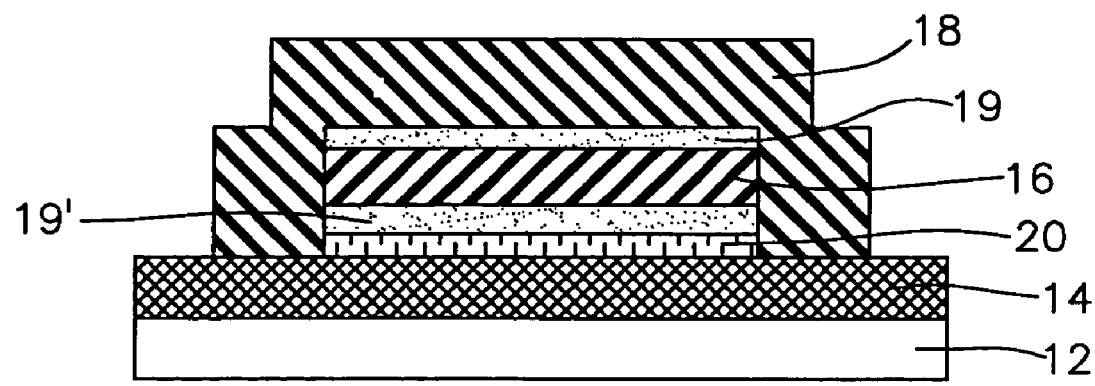
FIG. 14 is a schematic cross sectional view of the dressing of FIG. 12 including an additional spreading layer.

FIG. 14 is an adhesive wound dressing including two keying layers (19, 19') and a spreading layer (20) between the keying layer (19') and the adhesive layer (14).

Figure 15:
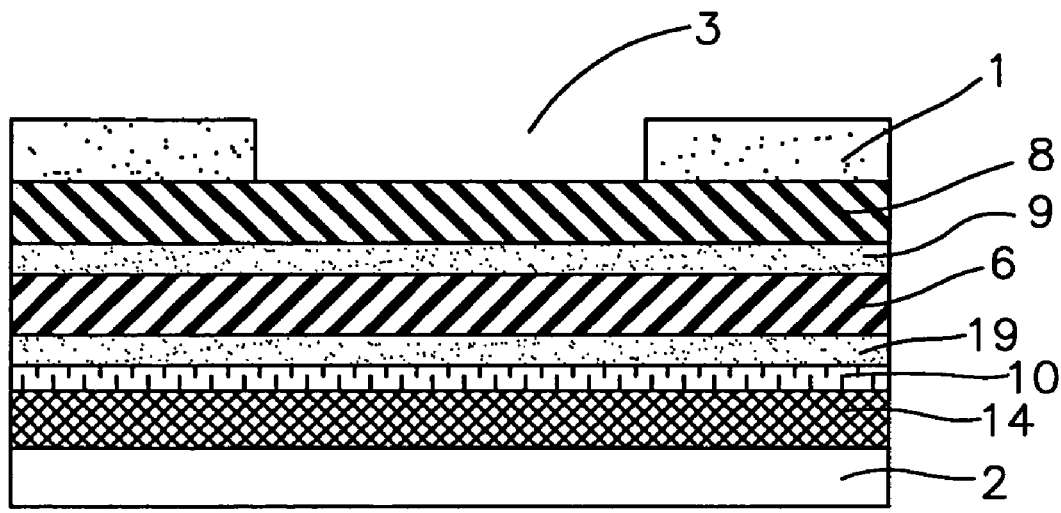
FIG. 15 is a schematic cross sectional view of the dressing of FIG. 9 including an additional adhesive layer

FIG. 15 is an adhesive version of the non-adhesive dressing depicted in FIG. 9. An additional adhesive layer (1) on the wound facing surface of the wound contacting layer (8) allows the dressing to be adhered to a patient. The adhesive layer (1) forms an band around the periphery of the wound facing surface of the dressing. The central area (3) of the dressing is free from adhesive and allows the wound contacting layer (8) to contact a wound in use.

Figure 16:
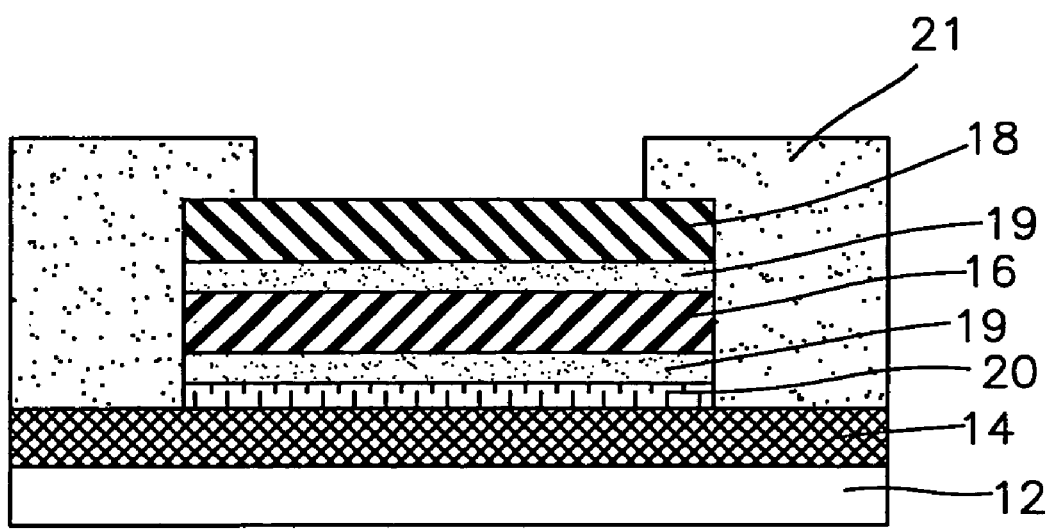
FIG. 16 is a schematic cross sectional view of the dressing of FIG. 14 including an additional adhesive layer

FIG. 16 is a modified version of the adhesive wound dressing of FIG. 14. The wound contacting layer (18) has the same surface area as each of the absorbent core (16), the two keying layers (19, 19') and the spread layer (20), all of which are smaller than the surface area of the adhesive layer (14) and the transmission layer (12). An additional adhesive layer (21) around the periphery of the dressing serves to provide the adhesive to adhere the dressing to the skin of a patient and helps maintain the structural integrity of the dressing.

The additional adhesive layer (1; 21) is a blend of one or more water soluble hydrocolloids and one or more low molecular weight polyisobutylenes. In an alternative embodiment the adhesive layer may be a polyamide web. The additional adhesive layer (1; 21) is thinner than the adhesive layer (4, 14), The dressing will typically be made in a range of sizes. For example, the non adhesive version may be made in the following sizes 7.5 mm by 7.5 mm, 10 mm by 10 mm, 15 mm by 15 mm and 15 mm by 20 mm. The adhesive version may be made in the following sizes 9 mm by 9 mm, 14 mm by 14 mm, 19 mm by 19 mm, 10 mm by 19 mm oval and shapes to include heel and sacral designs.

The dressing is placed on a wound, for example an ulcer, with the wound contacting layer in contact with the wound.

Wound dressings in accordance with the invention have a higher fluid handling capacity, even under compression, than known dressings. Typically compression is applied at about 40 mm Hg.

Wound dressings according to the invention with improved fluid handling capacity, low wicking and high MVTR also reduce maceration of the surrounding skin, help to prevent wound desiccation and have a longer wear time than known dressings.

The material used in the dressings, and the thickness of the dressings allows them to be more conformable and discrete in use than other known dressings.

To achieve such a combination of improvements over the known leading brands is surprising.

Comparative experiments have demonstrated the adhesive and non-adhesive versions of the present invention to have significant advantages.

Fluid retention studies have shown adhesive and non adhesive versions of wound dressings according to the present invention to have improved fluid retention properties. A wound dressing of the present invention comprising an absorbent core of 100% HYDROCEL™ displayed a fluid retention of 0.13 to 0.18 $g/cm^2$, compared to only 0.11 $g/cm^2$ in ALLEVYN™. The fluid retention studies were carried out under experimental conditions mimicking 40 mmHg compression.

Fluid handling studies have shown the adhesive and non adhesive versions of wound dressings according to the present invention to have improved fluid handling properties. A wound dressing of the present invention comprising an absorbent core of 100% HYDROCEL™ was able to handle 8 g of fluid per 10 $cm^2$ in a 24 hr period, which is significantly greater than competing products such as ALLEVYN™ which can handle only 4.5 g of fluid per 10 $cm^2$ in a 24 hr period.

By adjusting the fibre blend used in the absorbent core reduced shrinkage of the wound dressing upon fluid absorption was observed. In a dressing in which the absorbent core comprises 100% 200 gsm HYDROCEL™ 40% shrinkage in the surface area of the dressing was observed upon immersion in sodium chloride and calcium chloride solution (*BP 1995 Appendix 1A*). The level of shrinkage reduced to 21% when a blend of 75% 200 gsm HYDROCEL™ and 25% LYOCELL™ was used, and to 13% when the blend of 50% 200 gsm HYDROCEL™ and 50% LYOCELL™ was used. No significant change in absorption properties of the dressing was observed when a blend was used.

The invention claimed is:

1. A multi layered wound dressing for use on wounds producing high levels of exudate, the dressing comprising:
    a transmission layer having an MVTR of at least 300 $gm^2$/ 24 hours;
    an adhesive;
    an absorbent core comprising gel forming fibres and capable of absorbing and retaining exudates;
    a wound contacting layer comprising gel forming fibres and which transmits exudate to the absorbent core; and
    a keying layer positioned on the absorbent core and bonding the absorbent core to the wound contacting layer,
        the transmission layer overlying the adhesive which overlies the absorbent core and
        the absorbent core and wound contacting layer limiting the lateral spread of exudate in the dressing to the region of the wound.

2. The dressing according to claim 1 capable of handling at least 6 g of fluid per 10 $cm^2$ of dressing in 24 hours.

3. The dressing according to claim 2 capable of handling at between about 8 g and about 15 g of fluid per 10 $cm^2$ of dressing in 24 hours.

4. The dressing according to claim 1 in which the gel forming fibres of the wound contacting layer are chemically modified cellulosic fibres in the form of a fabric.

5. The dressing according to claim 4 in which the fibres are carboxymethylated cellulose fibres.

6. The dressing according to claim 1 in which the wound contact layer has a low lateral wicking rate from 5 mm per minute to 40 mm per minute.

7. The dressing according to claim 1 in which the wound contact layer has a fibre density between 25 $gm^2$ and 55 $gm^2$.

8. The dressing according to claim 7 in which the wound contact layer has a fibre density of 35 $gm^2$.

9. The dressing according to claim 1 wherein the absorbent core has an absorbency of exudate of at least 10 g/g.

10. The dressing according to claim 1 wherein the absorbent core has a rate of lateral wicking of less than 20 mm per minute.

11. The dressing according to claim 1 wherein the absorbent core is fibrous.

12. The dressing according to claim 11 wherein the fibre density in the absorbent core is between 150 $gm^2$ and 250 $gm^2$.

13. The dressing according to claim 12 wherein the density is approximately 200 $gm^2$.

14. The dressing according to claim 1 wherein the gel forming fibres of the absorbent core are sodium carboxymethylcellulose fibres.

15. The dressing according to claim 1 wherein the absorbent core is a blend of gel forming fibres and cellulosic fibres.

16. The dressing according to claim 15 wherein the absorbent core is a blend in the range of up to 25% cellulosic fibres by weight and 75% to 100% gel forming fibres by weight.

17. The dressing according to claim 15 wherein the blend is in the range of up to 50% cellulosic fibres by weight and 50% to 100% gel forming fibres by weight.

18. The dressing according to claim 17 wherein the blend is in the range of about 50% cellulosic fibres by weight and about 50% gel forming fibres by weight.

19. The dressing according to claim 1 wherein the keying layer is a polyamide web.

20. The dressing according to claim 1 wherein the transmission layer is a foam.

21. The dressing according to claim 1 wherein the transmission layer is a polyurethane foam laminated to a polyurethane film.

22. The dressing according to claim 1 including one or more layers selected from the group consisting of a soluble medicated film layer; an odour-absorbing layer; a spreading layer, and an additional adhesive layer.

23. The dressing according to claim 1 wherein the dressing is self-adhesive.

24. The dressing according to claim 1 wherein the dressing is non-self-adhesive.

25. The dressing according to claim 1 wherein the dressing is between 2 mm and 4 mm thick.

26. The dressing according to claim 1 wherein shrinkage of the dressing when wet is less than 25%.

* * * * *